United States Patent [19]

Yamamoto

[11] Patent Number: 4,732,995
[45] Date of Patent: Mar. 22, 1988

[54] NOVEL ISOCYANATE SILANE DERIVATIVES HAVING AT LEAST ONE TRIFLUOROETHOXY GROUP

[75] Inventor: Yasushi Yamamoto, Takasaki, Japan

[73] Assignee: Shin-Estu Chemical Co., Ltd., Japan

[21] Appl. No.: 63,532

[22] Filed: Jun. 18, 1987

[30] Foreign Application Priority Data

Jun. 19, 1986 [JP] Japan ................. 61-143514

[51] Int. Cl.$^4$ .................. C07F 7/10; C07F 7/18
[52] U.S. Cl. .................................. 556/414
[58] Field of Search ........................... 556/414

[56] References Cited

U.S. PATENT DOCUMENTS

| | | | |
|---|---|---|---|
| 3,458,554 | 7/1969 | Haluska | 556/414 X |
| 3,560,542 | 2/1971 | Kim et al. | 556/414 X |
| 4,543,404 | 9/1985 | Sugano et al. | 556/414 X |
| 4,654,428 | 3/1987 | Kurashima et al. | 556/414 |

*Primary Examiner*—Paul F. Shaver
*Attorney, Agent, or Firm*—Lowe, Price, LeBlanc, Becker & Shur

[57] ABSTRACT

A novel isocyanate silane derivative of the following formula

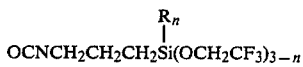

in which R represents an unsubstituted or substituted monovalent hydrocarbon group having from 1 to 8 carbon atoms, and n is a value of 0, 1 or 2.

7 Claims, 2 Drawing Figures

NOVEL ISOCYANATE SILANE DERIVATIVES HAVING AT LEAST ONE TRIFLUOROETHOXY GROUP

BACKGROUND OF THE INVENTION

Field of the Invention

This invention relates to a novel type of organic silicon compound which has been hitherto unknown in the art. More particularly, it relates to novel isocyanate silane derivatives which have at least one ready-to-hydrolyze trifluoroethoxy group in the molecule.

SUMMARY OF THE INVENTION

It is an object of the invention to provide a novel type of isocyanate silane derivative which has both an isocyanate group and at least one trifluoroethoxy group, which is ready to hydrolyze, in one molecule of the silane derivative.

It is another object of the invention to provide novel isocyanate silane derivatives which are highly compatible with fluorine-containing rubbers and resins because of the presence of the at least one trifluoroethoxy group.

It is a further object of the invention to provide novel isocyanate silane derivatives which are useful as a cross-linking agent for various coating compositions.

The above objects can be achieved, according to the invention, by an isocyanate silane derivative of the following general formula

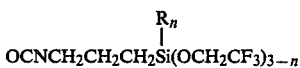

in which R represents an unsubstituted or substituted monovalent hydrocarbon group having from 1 to 8 carbon atoms, and n is a value of 0, 1 or 2.

DETAILED DESCRIPTION AND EMBODIMENTS OF THE INVENTION

Figure 1:
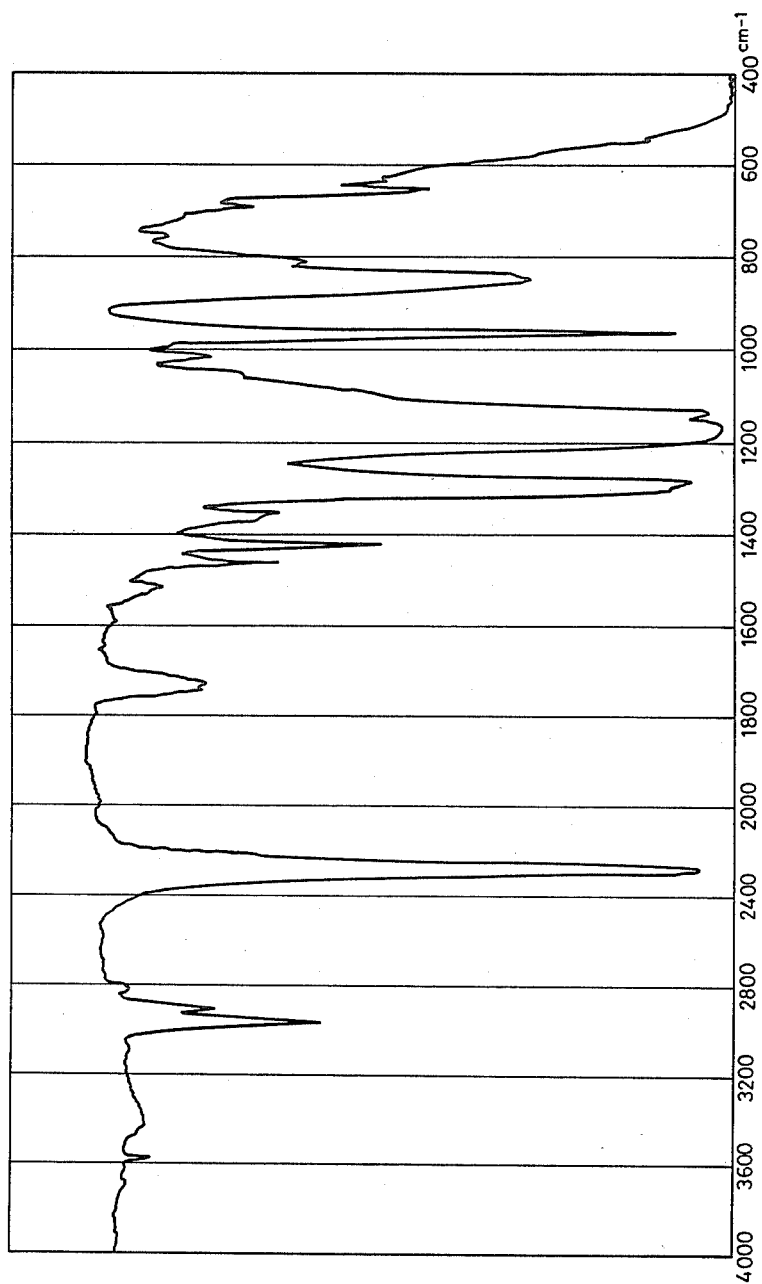
FIG. 1 is an IR absorption spectral curve of the isocyanate silane derivative obtained in Example 1.

In the above general formula representing the isocyanate silane derivatives or compounds according to the invention, R is an unsubstituted or substituted monovalent hydrocarbon group having from 1 to 8 carbon atoms as defined above, and each n is 0, 1 or 2. Specific examples of the monovalent hydrocarbon group include alkyl groups such as a methyl group, an ethyl group, a propyl group, a butyl group, a pentyl group, a hexyl group, a heptyl group and an octyl group, cycloalkyl groups such as a cyclohexyl group, alkenyl groups such as a vinyl group, an allyl group and the like, aryl groups such as a phenyl group, a tolyl group and the like, aralkyl groups such as a benzyl group and the like. Moreover, those groups indicated above may be partially or wholly substituted with a halogen atom, a cyano group and the like. Examples of such substituted groups include a chloromethyl group, a trifluoropropyl group, a cyanoethyl group, and the like.

In the above formula, it is preferred that n=0, or when n=1, R represents an alkyl group such as a methyl group. Most preferably, compounds of the following formulae (a) and (b) are used, which are, respectively, 3-tris(2,2,2-trifluoroethoxy)silylpropyl isocyanate and 3-bis(2,2,2,-trifluoroethoxy)-methylsilylpropyl isocyanate.

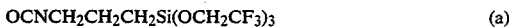

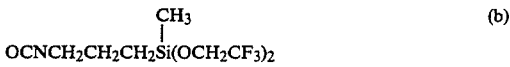

The isocyanate silane derivatives of the invention can be prepared according to the following reaction sequence in which triethylamine is added to an aminopropyl(trifluoroethoxy)silane compound, which is then reacted with phenyl chloroformate under ice-cooling conditions and further reacted with triorganochlorosilane under heating conditions.

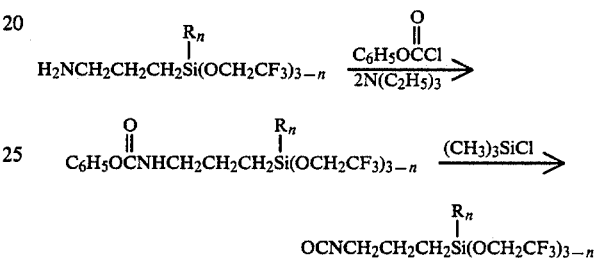

The phenyl chloroformate is added to the mixture under ice-cooling conditions and reacted with the silane compound generally at 10° to 70° C. for 1 to 5 hours. Thereafter, the reaction system is heated to a temperature of 40° to 70° C., to which the triorganochlorosilane is added, followed by further reaction at 80° to 110° C. for further 3 to 4 hours. By the reaction, triethylamine hydrochloride is secondarily produced. This hydrochloride is usually removed by filtration. These reactions are generally effected in an inert solvent. Examples of the solvent include aromatic hydrocarbons such as toluene, benzene, xylene, hexane and cyclohexanone.

The triethylamine in the above reactions is used to form a salt with secondarily produced hydrochloric acid, so that the reactions can proceed smoothly. Instead of triethylamine, other amines such as dimethyl-n-butylamine, dimethylethylamine, dimethylisopropylamine, pyridine, dimethylaniline and the like may be likewise used.

It will be noted that the starting aminopropyl(trifluoroethoxy)silane compound is prepared, for example, by reaction between 2,2,2-trifluoroethanol and 2-cyanoethylorganosilane, followed by hydrogenation in the presence of a Raney-cobalt catalyst. Various types of substituents represented by R may be readily introduced by suitably changing the above silane compound with other types of substituted silanes.

The final isocyanate silane derivatives have at least one trifluoroethoxy group which has a higher rate of hydrolysis than a methoxy or ethoxy group, and have also the isocyanate group. When the derivative is brought into contact with various types of polymers having active hydrogen groups such as $-NH_2$, $-NHR$, $-OH$, $-SH$ and the like, the active hydrogen group and the isocyanate group first react with each other. Subsequently, the trifluoroethoxy group hydrolyzes to cause the condensation reaction. This is why the silane derivatives of the invention are more useful as a curing agent for various materials than known isocyanate compounds used for these purposes.

Moreover, because of the high rate of hydrolysis of the trifluoroethoxy group, the silane derivatives of the invention are readily compatible with a variety of fluorine compounds or polymers. Although 2,2,2-trifluoroethanol is secondarily produced by the hydrolysis, it does not cause the system opaque, so that the silane derivatives are also useful as a coating paint, a crosslinking agent for coating materials, and an adhesive.

In view of the ease in preparation and the excellence in properties, the silane silane compounds of the aforeindicated formulae (a) and (b) are most preferable.

The present invention is described in more detail by way of examples.

EXAMPLE 1

38.3 g of 3-aminopropyltris(2,2,2-trifluoroethoxy)silane and 23.3 g of triethylamine were dissolved in 150 ml of toluene, into which 15.7 g of phenyl chloroformate was dropped under ice-cooling conditions. After completion of the dropping, the reaction mixture was heated to 40° to 50° C. at which the reaction was carried out for 2 hours. Thereafter, the reaction mixture was further heated to 60° to 80° C., into which 11.5 g of trimethylchlorosilane was dropped, followed by reaction at a temperature of from 100° to 110° C. for 3 hours under agitation, during which triethylamine hydrochloride was secondarily produced. The thus produced hydrochloride was removed by filtration and the filtrate was distilled. After recovery of the toluene, a fraction of 88° to 89° C./3 mmHg was obtained in an amount of 28.6 g (yield 76%). This fraction was subjected to an elementary analysis, a gas mass spectrometry, and infrared absorption and NMR spectral analyses, with the following results. From these results, the product was found to be 3-tris(2,2,2-trifluoroethoxy)silylpropyl isocyanate of the following formula $$OCNCH_2CH_2CH_2Si(OCH_2CF_3)_3$$

Elementary analysis:

|  | C | H | Si | F |
|---|---|---|---|---|
| calculated for $C_{10}H_{12}F_9NO_4Si$ (%) | 29.34 | 2.96 | 6.86 | 41.78 |
| found | 29.31 | 2.98 | 6.84 | 41.80 |

Molecular weight: 409 (gas mass spectrometric).

IR absorption spectrum: see FIG. 1. 2,275 cm$^{-1}$ (S, NCO).

NMR spectrum (CCl$_4$, internal standard C$_6$H$_6$): 0.45–0.62 (m, 2H, Si—CH$_2$—C), 1.28–1.63 (m, 2H, C—CH$_2$—C), 3.10–3.23 (t, 2H, —C—CH$_2$NCO), 3.88–4.16 (q, 6H, SiOCH$_2$CF$_3$).

EXAMPLE 2

29.9 g of 3-aminopropylmethylbis(2,2,2-trifluoroethoxy)silane and 23.3 g of triethylamine were dissolved in 150 ml of toluene, followed by reaction with 15.7 g of phenyl chloroformate in the same manner as in Example 1 and subsequent treatment with 11.5 g of trimethylchlorosilane. The resultant triethylamine hydrochloride was removed by filtration and the filtrate was distilled to obtain 22.1 g (yield 68%) of a fraction having a boiling point of 88° C./4 mmHg. This product was subjected to an elementary analysis, a gas mass spectrometry and IR and NMR spectral analyses in the same manner as in Example 1. From the results, the product was found to be 3-bis(2,2,2-trifluoroethoxy)methylsilylpropyl isocyanate of the following formula $$\begin{array}{c} CH_3 \\ | \\ OCNCH_2CH_2CH_2Si(OCH_2CF_3)_2 \end{array}$$

Elementary analysis:

|  | C | H | Si | F |
|---|---|---|---|---|
| calculated for $C_{19}H_{13}F_6NO_3Si$ (%) | 33.23 | 4.04 | 8.63 | 35.04 |
| found | 33.20 | 4.08 | 8.60 | 35.07 |

Molecular weight: 325 (gas mass spectrometric).

Figure 2:
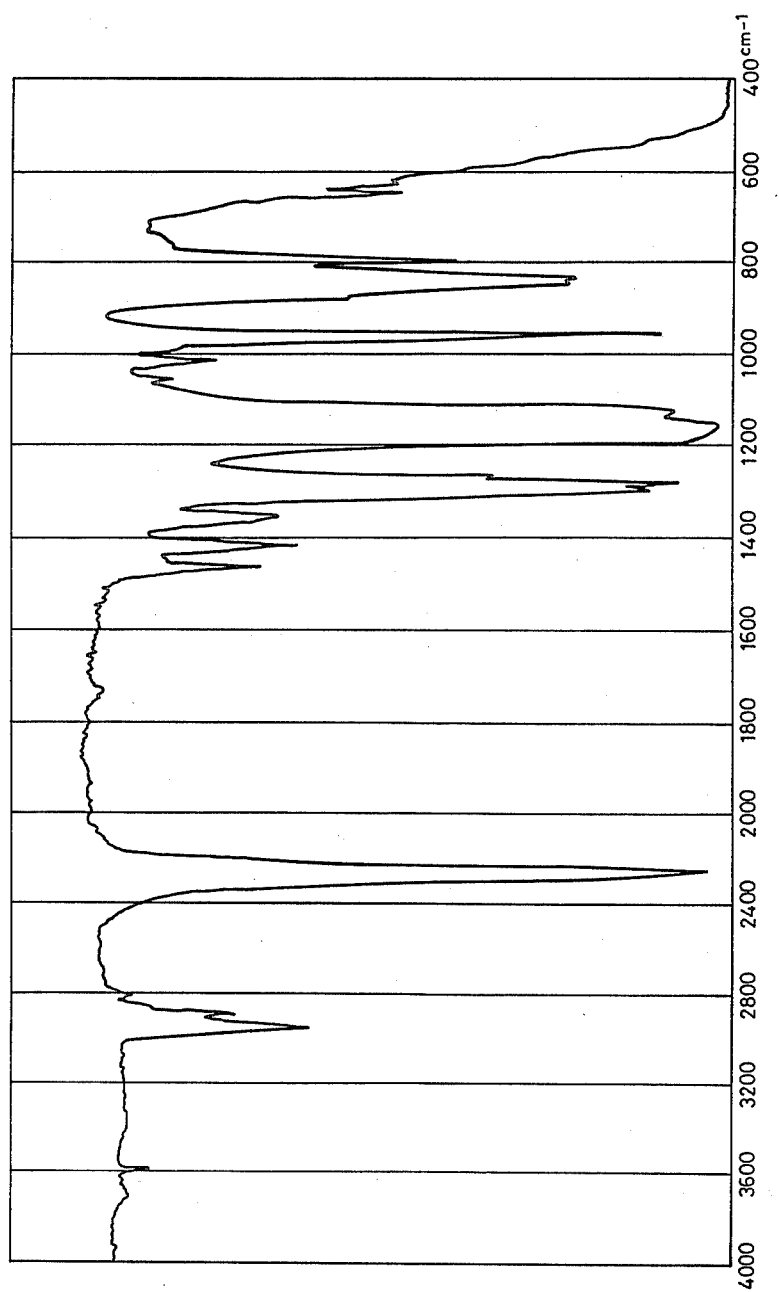
FIG. 2 is similar to FIG. 1, but the silane derivative used is obtained in Example 2.

IR absorption spectrum: see FIG. 2. 2,275 cm$^{-1}$ (S, —NCO).

NMR spectrum (CCl$_4$, internal standard C$_6$H$_6$): −0.32 (S, 3H, SiCH$_3$), 0.07–0.38 (m, 2H, SiCH$_2$C), 1.03–1.45 (m, 2H, CCH$_2$C), 2.95–3.08 (t, 2H, C—CH$_2$—NCO), 3.67–3.94 (q, 4H, —SiOCH$_2$CF$_3$).

EXAMPLE 3

The general procedure of Example 1 was repeated using, instead of 38.3 g of 3-aminopropyltris(2,2,2-trifluoroethoxy)silane, 31.1 g of 3-aminopropylvinylbis(2,2,2-trifluoroethoxy)silane, 36.1 g of 3-aminopropylphenylbis(2,2,2-trifluoroethoxy)silane, 37.5 g of 3-aminopropylbenzylbis(2,2,2-trifluoroethoxy)silane, 38.1 g of 3-aminotrifluoropropylbis-(2,2,2-trifluoroethoxy)silane, thereby obtaining 22.0 g of 3-bis(2,2,2-trifluoroethoxy)vinylsilylpropyl isocyanate, 28.0 g of 3-bis(2,2,2-trifluoroethoxy)phenylsilylpropyl isocyanate, 22.0 g of 3-bis(2,2,2-trifluoroethoxy)benzylsilylpropyl isocyanate, and 28.0 g of 3-bis(2,2,2-trifluoroethoxy)trifluoropropylsilylpropyl isocyanate. The formation of these compounds was confirmed in the same manner as in Example 1.

What is claimed is:

1. A isocyanate silane derivative of the following general formula $$\begin{array}{c} R_n \\ | \\ OCNCH_2CH_2CH_2Si(OCH_2CF_3)_{3-n} \end{array}$$

in which R represents an unsubstituted or substituted monovalent hydrocarbon group having from 1 to 8 carbon atoms, and n is a value of 0, 1 or 2.

2. An isocyanate silane derivative according to claim 1 wherein n is 0.

3. An isocyanate silane derivative according to claim 1, wherein n is 1.

4. An isocyanate silane derivative according to claim 1, wherein n is 2.

5. An isocyanate silane derivative according to claim 1, wherein R represents an alkyl group and n=1.

6. An isocyanate silane derivative according to claim 1, wherein said derivative is 3-tris(2,2,2-trifluoroethoxy)silylpropyl isocyanate of the formula $$OCNCH_2CH_2CH_2Si(OCH_2CF_3)_3.$$

7. An isocyanate silane derivative according to claim 1, wherein said derivative is 3-bis(2,2,2-trifluoroethoxy)methylsilylpropyl isocyanate of the formula $$\begin{array}{c} CH_3 \\ | \\ OCNCH_2CH_2CH_2Si(OCH_2CF_3)_2 \end{array}$$

* * * * *